US009161772B2

(12) United States Patent
Hyodo

(10) Patent No.: US 9,161,772 B2
(45) Date of Patent: Oct. 20, 2015

(54) SURGICAL INSTRUMENT AND MEDICAL MANIPULATOR

(75) Inventor: Ryoji Hyodo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 353 days.

(21) Appl. No.: 13/566,023

(22) Filed: Aug. 3, 2012

(65) Prior Publication Data
US 2013/0066333 A1 Mar. 14, 2013

Related U.S. Application Data

(60) Provisional application No. 61/515,203, filed on Aug. 4, 2011.

(51) Int. Cl.
*A61B 17/00* (2006.01)
*A61B 17/29* (2006.01)
(Continued)

(52) U.S. Cl.
CPC ........... *A61B 17/29* (2013.01); *A61B 17/32002* (2013.01); *A61B 18/1402* (2013.01); *A61B 19/081* (2013.01); *A61B 19/22* (2013.01); *A61B 19/2203* (2013.01); *A61B 19/26* (2013.01); *A61B 19/44* (2013.01); *B25J 13/02* (2013.01); *G06F 3/01* (2013.01); *A61B 17/068* (2013.01);
(Continued)

(58) Field of Classification Search
CPC ................. A61B 17/068; A61B 17/29; A61B 2017/00473; A61B 2014/00482; A61B 2017/2931; A61B 2017/2946; A61B 18/1402; Y10S 901/30

USPC ........... 606/1, 51–52, 130, 205–209; 600/104
See application file for complete search history.

(56) References Cited

U.S. PATENT DOCUMENTS 4,830,569 A * 5/1989 Jannborg ...................... 414/729
5,214,969 A 6/1993 Adkins et al.
(Continued)

FOREIGN PATENT DOCUMENTS

| CN | 101167658 A | 4/2008 |
|----|-------------|--------|
| CN | 101426412 A | 5/2009 |

(Continued)

OTHER PUBLICATIONS

International Search Report dated Oct. 23, 2012 from related International Application No. PCT/JP2012/070414.
(Continued)

*Primary Examiner* — David Eastwood
(74) *Attorney, Agent, or Firm* — Scully, Scott, Murphy & Presser, P.C.

(57) ABSTRACT

A surgical instrument for performing treatment to a treatment target portion includes a cylindrical elongated member; a treatment part, and a connection part. The connection part includes a first turning axis part provided to the elongated member, a second turning axis part provided to the treatment part, a first rolling guide part that is provided to the elongated member and includes a circular-arc-shaped part coaxial with the first turning axis part, a second rolling guide part that is provided to the treatment part and includes a rolling guide part including a circular-arc-shaped part coaxial with the second turning axis part, the rolling guide part rollingly contacting the first rolling guide part, and an engaging part that brings the treatment part and the elongated member into an engaging state. The connection part is detachable between the first turning axis part and the second turning axis part.

11 Claims, 14 Drawing Sheets

(51) Int. Cl.
*A61B 17/32* (2006.01)
*A61B 18/14* (2006.01)
*A61B 19/08* (2006.01)
*A61B 19/00* (2006.01)
*B25J 13/02* (2006.01)
*G06F 3/01* (2006.01)
A61B 17/068 (2006.01)
A61B 19/10 (2006.01)

(52) U.S. Cl.
CPC .............. *A61B 19/10* (2013.01); *A61B 19/5244* (2013.01); *A61B 19/56* (2013.01); *A61B 2017/00119* (2013.01); *A61B 2017/00473* (2013.01); *A61B 2017/00477* (2013.01); *A61B 2017/00482* (2013.01); *A61B 2017/2931* (2013.01); *A61B 2017/2946* (2013.01); *A61B 2019/2223* (2013.01); *A61B 2019/2234* (2013.01); *A61B 2019/2269* (2013.01); *A61B 2019/2292* (2013.01); *A61B 2019/2296* (2013.01); *A61B 2019/465* (2013.01); *A61B 2019/467* (2013.01); *A61B 2019/4815* (2013.01); *A61B 2019/4868* (2013.01); *A61B 2019/4873* (2013.01); *A61B 2019/5255* (2013.01); *A61B 2019/5289* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | | |
|---|---|---|---|---|
| 5,603,723 | A * | 2/1997 | Aranyi et al. | 606/205 |
| 5,632,432 | A | 5/1997 | Schulze et al. | |
| 5,649,956 | A | 7/1997 | Jensen et al. | |
| 5,656,903 | A | 8/1997 | Shui et al. | |
| 5,712,543 | A | 1/1998 | Sjostrom | |
| 5,762,458 | A | 6/1998 | Wang et al. | |
| 5,836,869 | A | 11/1998 | Kudo et al. | |
| 5,855,583 | A | 1/1999 | Wang et al. | |
| 5,871,493 | A | 2/1999 | Sjostrom et al. | |
| 6,007,550 | A | 12/1999 | Wang et al. | |
| 6,063,095 | A | 5/2000 | Wang et al. | |
| 6,090,122 | A | 7/2000 | Sjostrom et al. | |
| 6,102,850 | A | 8/2000 | Wang et al. | |
| 6,132,368 | A | 10/2000 | Cooper | |
| 6,132,441 | A | 10/2000 | Grace | |
| 6,206,903 | B1 | 3/2001 | Ramans | |
| 6,246,200 | B1 | 6/2001 | Blumenkranz et al. | |
| 6,328,752 | B1 | 12/2001 | Sjostrom et al. | |
| 6,346,072 | B1 | 2/2002 | Cooper | |
| 6,430,473 | B1 | 8/2002 | Lee et al. | |
| 6,436,107 | B1 | 8/2002 | Wang et al. | |
| 6,441,577 | B2 | 8/2002 | Blumenkranz et al. | |
| 6,557,558 | B1 | 5/2003 | Tajima et al. | |
| 6,574,355 | B2 | 6/2003 | Green | |
| 6,587,750 | B2 | 7/2003 | Gerbi et al. | |
| 6,602,185 | B1 | 8/2003 | Uchikubo | |
| 6,645,196 | B1 | 11/2003 | Nixon et al. | |
| 6,666,876 | B2 | 12/2003 | Kawai et al. | |
| 6,676,684 | B1 * | 1/2004 | Morley et al. | 606/205 |
| 6,685,698 | B2 * | 2/2004 | Morley et al. | 606/1 |
| 6,699,177 | B1 | 3/2004 | Wang et al. | |
| 6,746,443 | B1 * | 6/2004 | Morley et al. | 606/1 |
| 6,783,524 | B2 | 8/2004 | Anderson et al. | |
| 6,853,879 | B2 | 2/2005 | Sunaoshi | |
| 6,866,671 | B2 | 3/2005 | Tierney et al. | |
| 6,905,460 | B2 | 6/2005 | Wang et al. | |
| 6,913,613 | B2 * | 7/2005 | Schwarz et al. | 606/206 |
| 7,083,571 | B2 | 8/2006 | Wang et al. | |
| 7,101,363 | B2 * | 9/2006 | Nishizawa et al. | 606/1 |
| 7,107,124 | B2 | 9/2006 | Green | |
| 7,118,582 | B1 | 10/2006 | Wang et al. | |
| 7,273,488 | B2 | 9/2007 | Nakamura et al. | |
| 7,295,893 | B2 | 11/2007 | Sunaoshi | |
| 7,313,464 | B1 | 12/2007 | Perreault et al. | |
| 7,331,967 | B2 | 2/2008 | Lee et al. | |
| 7,357,774 | B2 * | 4/2008 | Cooper | 600/102 |
| 7,422,592 | B2 * | 9/2008 | Morley et al. | 606/51 |
| 7,476,237 | B2 | 1/2009 | Taniguchi et al. | 606/205 |
| 7,549,998 | B2 | 6/2009 | Braun | 606/205 |
| 7,608,083 | B2 * | 10/2009 | Lee et al. | 606/130 |
| 7,654,431 | B2 * | 2/2010 | Hueil et al. | 227/175.1 |
| 7,666,191 | B2 | 2/2010 | Orban, III et al. | |
| 7,674,255 | B2 * | 3/2010 | Braun | 606/1 |
| 7,695,481 | B2 | 4/2010 | Wang et al. | |
| 7,699,835 | B2 * | 4/2010 | Lee et al. | 606/1 |
| 7,699,855 | B2 | 4/2010 | Anderson et al. | |
| 7,778,733 | B2 | 8/2010 | Nowlin et al. | |
| 7,819,884 | B2 * | 10/2010 | Lee et al. | 606/130 |
| 7,819,885 | B2 | 10/2010 | Cooper | |
| 7,862,579 | B2 * | 1/2011 | Ortiz et al. | 606/205 |
| 7,865,266 | B2 | 1/2011 | Moll et al. | |
| 7,955,321 | B2 * | 6/2011 | Kishi et al. | 606/1 |
| 8,105,320 | B2 * | 1/2012 | Manzo | 606/1 |
| 8,155,479 | B2 | 4/2012 | Hoffman et al. | |
| 8,267,958 | B2 * | 9/2012 | Braun | 606/205 |
| 8,350,806 | B2 | 1/2013 | Nagasaka et al. | |
| 8,423,186 | B2 | 4/2013 | Itkowitz et al. | |
| 8,496,647 | B2 * | 7/2013 | Blumenkranz et al. | 606/1 |
| 8,540,748 | B2 * | 9/2013 | Murphy et al. | 606/205 |
| 8,845,681 | B2 * | 9/2014 | Grace | 606/205 |
| 8,876,858 | B2 * | 11/2014 | Braun | 606/205 |
| 8,903,549 | B2 | 12/2014 | Itkowitz et al. | |
| 8,906,002 | B2 * | 12/2014 | Kishi et al. | 606/1 |
| 2001/0021859 | A1 | 9/2001 | Kawai et al. | |
| 2001/0055062 | A1 | 12/2001 | Shioda et al. | |
| 2002/0072736 | A1 | 6/2002 | Tierney et al. | |
| 2002/0091374 | A1 | 7/2002 | Cooper | |
| 2002/0128552 | A1 | 9/2002 | Nowlin et al. | |
| 2003/0033024 | A1 | 2/2003 | Sunaoshi | |
| 2003/0060927 | A1 | 3/2003 | Gerbi et al. | |
| 2003/0069471 | A1 | 4/2003 | Nakanishi et al. | |
| 2003/0083648 | A1 | 5/2003 | Wang et al. | |
| 2003/0100817 | A1 | 5/2003 | Wang et al. | |
| 2003/0216723 | A1 | 11/2003 | Shinmura et al. | |
| 2004/0092912 | A1 | 5/2004 | Jinno et al. | |
| 2004/0111113 | A1 * | 6/2004 | Nakamura et al. | 606/205 |
| 2004/0140787 | A1 | 7/2004 | Okamoto et al. | |
| 2004/0186345 | A1 | 9/2004 | Yang et al. | |
| 2004/0186624 | A1 | 9/2004 | Oda et al. | |
| 2004/0243147 | A1 | 12/2004 | Lipow | |
| 2005/0020876 | A1 | 1/2005 | Shioda et al. | |
| 2005/0021050 | A1 | 1/2005 | Cooper | |
| 2005/0033117 | A1 | 2/2005 | Ozaki et al. | |
| 2005/0125027 | A1 | 6/2005 | Knodel et al. | |
| 2005/0149003 | A1 | 7/2005 | Tierney et al. | |
| 2005/0228365 | A1 | 10/2005 | Wang et al. | |
| 2005/0273086 | A1 | 12/2005 | Green et al. | |
| 2006/0052664 | A1 | 3/2006 | Julian et al. | |
| 2006/0074408 | A1 | 4/2006 | Jinno et al. | |
| 2006/0079865 | A1 | 4/2006 | Jinno et al. | |
| 2006/0079866 | A1 | 4/2006 | Jinno et al. | |
| 2006/0087746 | A1 | 4/2006 | Lipow | |
| 2006/0116973 | A1 | 6/2006 | Okamoto et al. | |
| 2006/0155262 | A1 * | 7/2006 | Kishi et al. | 606/1 |
| 2006/0161138 | A1 | 7/2006 | Orban, III et al. | |
| 2006/0190031 | A1 * | 8/2006 | Wales et al. | 606/205 |
| 2006/0235436 | A1 | 10/2006 | Anderson et al. | |
| 2007/0012135 | A1 | 1/2007 | Tierney et al. | |
| 2007/0089557 | A1 | 4/2007 | Solomon et al. | |
| 2007/0119274 | A1 | 5/2007 | Devengenzo et al. | |
| 2007/0137372 | A1 | 6/2007 | Devengenzo et al. | |
| 2007/0167679 | A1 | 7/2007 | Miyamoto et al. | |
| 2007/0167680 | A1 | 7/2007 | Miyamoto et al. | |
| 2007/0173689 | A1 | 7/2007 | Ozaki et al. | |
| 2007/0197896 | A1 | 8/2007 | Moll et al. | |
| 2007/0208375 | A1 * | 9/2007 | Nishizawa et al. | 606/205 |
| 2007/0219668 | A1 | 9/2007 | Takahashi et al. | |
| 2007/0225550 | A1 | 9/2007 | Gattani et al. | |
| 2007/0249897 | A1 | 10/2007 | Miyamoto et al. | |
| 2007/0265638 | A1 | 11/2007 | Lipow | |

(56) References Cited

U.S. PATENT DOCUMENTS

| | | |
|---|---|---|
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi et al. |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi et al. |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0230894 A1 | 9/2011 | Simaan et al. |
| 2011/0238079 A1 | 9/2011 | Hannaford et al. |
| 2011/0282493 A1 | 11/2011 | Ortmaier |
| 2011/0288579 A1 | 11/2011 | Hyodo |
| 2012/0165828 A1* | 6/2012 | Duque et al. ............... 606/130 |
| 2012/0191245 A1 | 7/2012 | Fudaba et al. |

FOREIGN PATENT DOCUMENTS

| | | |
|---|---|---|
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-29810 A | 2/1988 |
| JP | 64-34688 A | 2/1989 |
| JP | 1-271185 A | 10/1989 |
| JP | 2-71980 A | 3/1990 |
| JP | 2-292193 A | 12/1990 |
| JP | 3-161289 A | 7/1991 |
| JP | 5-96477 A | 4/1993 |
| JP | 5-329784 A | 12/1993 |
| JP | 7-1366 A | 1/1995 |
| JP | 7-194609 A | 8/1995 |
| JP | 7-241300 A | 9/1995 |
| JP | 7-246578 A | 9/1995 |
| JP | 7-96182 B2 | 10/1995 |
| JP | 8-66883 A | 3/1996 |
| JP | 8-215204 A | 8/1996 |
| JP | 8-243080 A | 9/1996 |
| JP | 10-128538 A | 5/1998 |
| JP | 11-300662 A | 11/1999 |
| JP | 2000-312684 A | 11/2000 |
| JP | 2001-113481 A | 4/2001 |
| JP | 2001-277157 A | 10/2001 |
| JP | 2001-309920 A | 11/2001 |
| JP | 2002-14287 A | 1/2002 |
| JP | 2002-59380 A | 2/2002 |
| JP | 2002-102248 A | 4/2002 |
| JP | 2002-272758 A | 9/2002 |
| JP | 2002-537884 A | 11/2002 |
| JP | 2003-24336 A | 1/2003 |
| JP | 2003-53685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-312991 A | 11/2005 |
| JP | 2006-61272 A | 3/2006 |
| JP | 2006-167867 A | 6/2006 |
| JP | 2006-288955 A | 10/2006 |
| JP | 2006-321027 A | 11/2006 |
| JP | 2007-29274 A | 2/2007 |
| JP | 2007-38315 A | 2/2007 |
| JP | 2007-98507 A | 4/2007 |
| JP | 2007-105485 A | 4/2007 |
| JP | 3999816 B2 | 10/2007 |
| JP | 2008-282 A | 1/2008 |
| JP | 2008-36793 A | 2/2008 |
| JP | 4058113 B2 | 3/2008 |
| JP | 2008-93270 A | 4/2008 |
| JP | 2008-173724 A | 7/2008 |
| JP | 4129313 B2 | 8/2008 |
| JP | 4176126 B2 | 11/2008 |
| JP | 2009-028157 A | 2/2009 |
| JP | 2009-56164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |
| JP | 2010-76012 A | 4/2010 |
| JP | 2010-524548 A | 7/2010 |
| JP | 2011-509112 A | 3/2011 |
| JP | 2001-087281 A | 4/2011 |
| JP | 2001-277157 A | 10/2011 |
| JP | 2011-206213 A | 10/2011 |
| JP | 2012-12104 A | 1/2012 |
| JP | 2012-91310 A | 5/2012 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | 00/51486 A1 | 9/2000 |
| WO | 00/60421 A2 | 10/2000 |
| WO | 03/049596 A2 | 6/2003 |
| WO | WO 2007/047782 A2 | 4/2007 |
| WO | 2007/075864 A1 | 7/2007 |

(56) References Cited

FOREIGN PATENT DOCUMENTS

| WO | WO 2007/111955 A2 | 10/2007 |
|---|---|---|
| WO | WO 2007/126443 A2 | 11/2007 |
| WO | 2007/138674 A1 | 12/2007 |
| WO | 2008/038184 A2 | 4/2008 |
| WO | 2008/108289 A1 | 9/2008 |
| WO | 2009/034477 A2 | 3/2009 |
| WO | 2009-089614 A1 | 7/2009 |
| WO | 2010/006057 A1 | 1/2010 |
| WO | 2010/109932 A1 | 9/2010 |
| WO | 2011/060139 A2 | 5/2011 |
| WO | 2011/060185 A1 | 5/2011 |
| WO | 2011/085815 A1 | 7/2011 |
| WO | WO 2012/042949 A1 | 4/2012 |

OTHER PUBLICATIONS

International Search Report dated Sep. 4, 2012 from related International Application No. PCT/JP2012/070408.
International Search Report dated Aug. 28, 2012 from related International Application No. PCT/JP2012/069927.
International Search Report dated Sep. 4, 2012 from related International Application No. PCT/JP2012/070415.
International Search Report dated Oct. 16, 2012 from related International Application No. PCT/JP2012/070581.
International Search Report dated Nov. 13, 2012 from related International Application No. PCT/JP2012/070576.
International Search Report dated Sep. 18, 2012 from related International Application No. PCT/JP2012/070417.
International Search Report dated Oct. 30, 2012 from related International Application No. PCT/JP2012/070418.
International Search Report dated Sep. 11, 2012 from related International Application No. PCT/JP2012/070416.
International Search Report dated Sep. 18, 2012 from related International Application No. PCT/JP2012/070407.
International Search Report dated Sep. 18, 2012 from related International Application No. PCT/JP2012/069868.
International Search Report dated Nov. 6, 2012 from related International Application No. PCT/JP2012/069919.
International Search Report dated Sep. 11, 2012 from related International Application No. PCT/JP2012/069696.
English language abstract only of JP 01-234140 published Sep. 19, 1989.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0666.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
U.S. Office Action dated Apr. 9, 2015 received in related U.S. Appl. No. 14/169,675.
Office Action dated May 8, 2015 received in related U.S. Appl. No. 14/157,920.
Chinese Office Action dated Jul. 1, 2015 from related Chinese Application No. 201280037244.6, together with an English language translation.

\* cited by examiner

SURGICAL INSTRUMENT AND MEDICAL MANIPULATOR

Priority is claimed on U.S. Provisional Patent Application No. 61/515,203 filed Aug. 4, 2011, the content of which is incorporated herein by reference.

BACKGROUND OF THE INVENTION

1. Field of the Invention

The present invention relates to a surgical instrument and a medical manipulator.

2. Description of Related Art

A conventionally known medical manipulator is a master-slave type medical manipulator including a master manipulator operated by an operator and a slave manipulator that operates on the basis of signals sent from the master manipulator. A surgical instrument has a treatment part for treating a treatment target portion by remote-control operation, and is attached to the medical manipulator.

For example, Japanese Unexamined Patent Application, First Publication No. 2001-277157 discloses a medical manipulator that enables a plurality of treatment parts appropriate for treatment to be switchingly attached to the arm of one slave manipulator.

SUMMARY OF THE INVENTION

According to a first aspect of the present invention, a surgical instrument for performing treatment to a treatment target portion includes: a cylindrical elongated member with a long axis, a treatment part connected to the elongated member, and a connection part that detachably connects the elongated member to the treatment part. The connection part includes a first turning axis part provided to the elongated member, a second turning axis part provided to the treatment part, a first rolling guide part that is provided to the elongated member and includes a circular-arc-shaped part coaxial with the first turning axis part, a second rolling guide part that is provided to the treatment part and includes a rolling guide part having a circular-arc-shaped part coaxial with the second turning axis part, the rolling guide part rollingly contacting the first rolling guide part, and an engaging part that brings the treatment part and the elongated member into an engaging state. The connection part is detachable between the first turning axis part and the second turning axis part.

The engaging part may include a main unit that is connected to the first turning axis part and is capable of engaging with the second turning axis part, a ring-shaped member that is provided separately from the main unit, and binds the main unit together with the second turning axis part, and a locking member that switches between a bound state and a released state, wherein in the bound state, the ring-shaped member is arranged in a position where it binds the main unit and the second turning axis part, and in the released state, the ring-shaped member is arranged in a position deviated from the position where it binds the main unit and the second turning axis part.

The main unit may include a groove that engages with the ring-shaped member and defines its movement direction. The locking member may include a groove and is capable of moving relative to the main unit. When the groove provided in the ring-shaped member and the groove provided in the main unit are in a communicating state, the locking member is capable of switching between the bound state and the released state. When the groove provided in the locking member and the groove provided in the main unit are in a non-communicating state, the treatment part is held in the bound state with respect to the elongated member.

The surgical instrument of the above aspect may further include: a treatment tool piece provided on the treatment part and is capable of operating, a joint for operating treatment tool piece that connects the elongated member to the treatment tool piece, and a moving member that is connected to the joint for operating treatment tool piece in order to operate the treatment tool piece. The joint for operating treatment tool piece may include a first operation turning member that is connected to the moving member and turns around a predetermined center of turning, a second operation turning member that is connected to the first operation turning member such that it turns in the opposite direction relative to the first operation turning member coaxial with the second turning axis part or around a center of turning that is nearer to the first turning axis part than the second turning axis part, and a link that converts the rotational force of the second operation turning member to an operation of the treatment tool piece. The joint for operating treatment tool piece is detachable between the first operation turning member and the second operation turning member by being detachable from the connection part.

The surgical instrument may include a pair of the treatment tool pieces, the operation of the treatment tool pieces being an operation of opening and closing them.

According to a second aspect of the present invention, a medical manipulator includes: the surgical instrument described above, a slave manipulator including at least one joint, the surgical instrument being attached to the slave manipulator, and a master manipulator that sends operating commands for driving the joint of the slave manipulator.

DETAILED DESCRIPTION OF THE INVENTION

Figure 1:
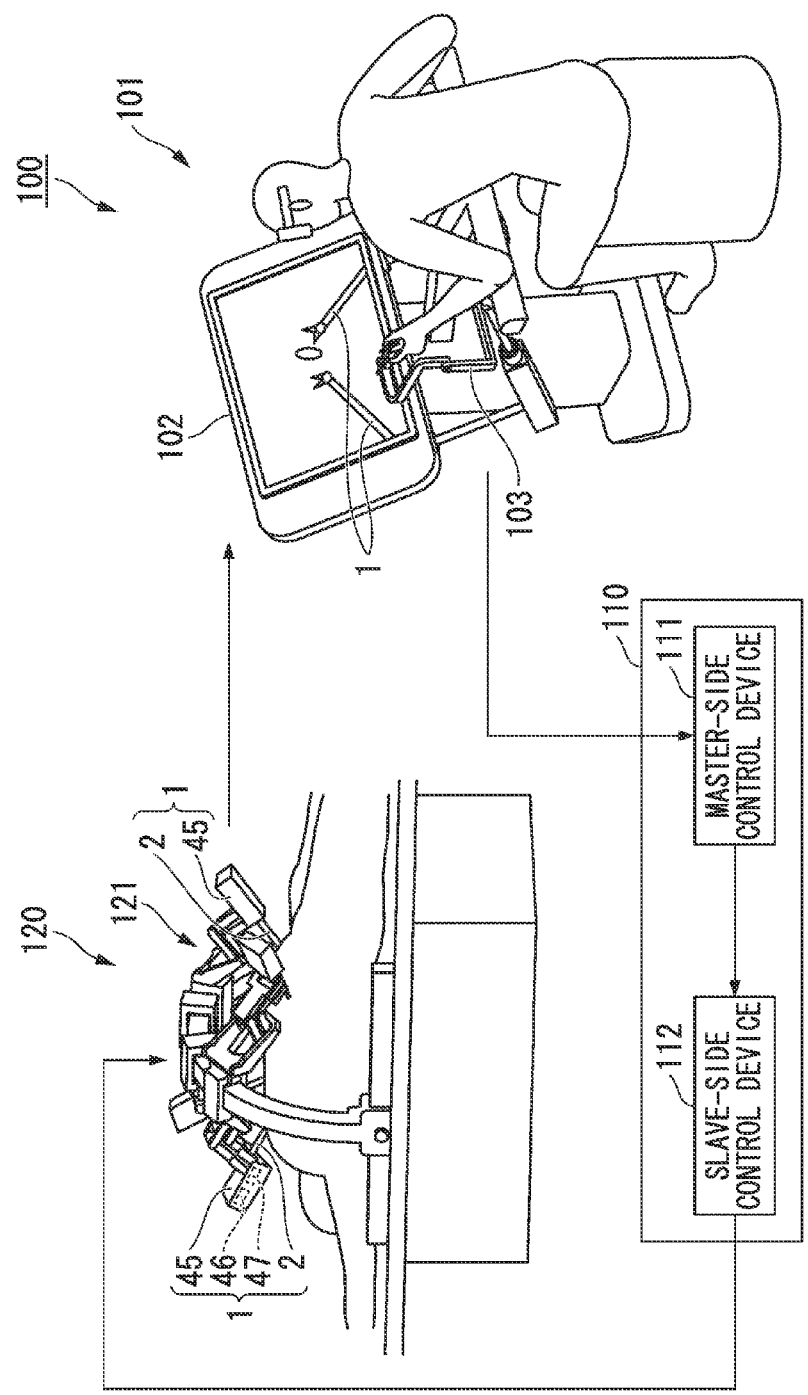
FIG. 1 is an overall view of a medical manipulator including a surgical instrument according to one embodiment of the present invention.
Figure 2:
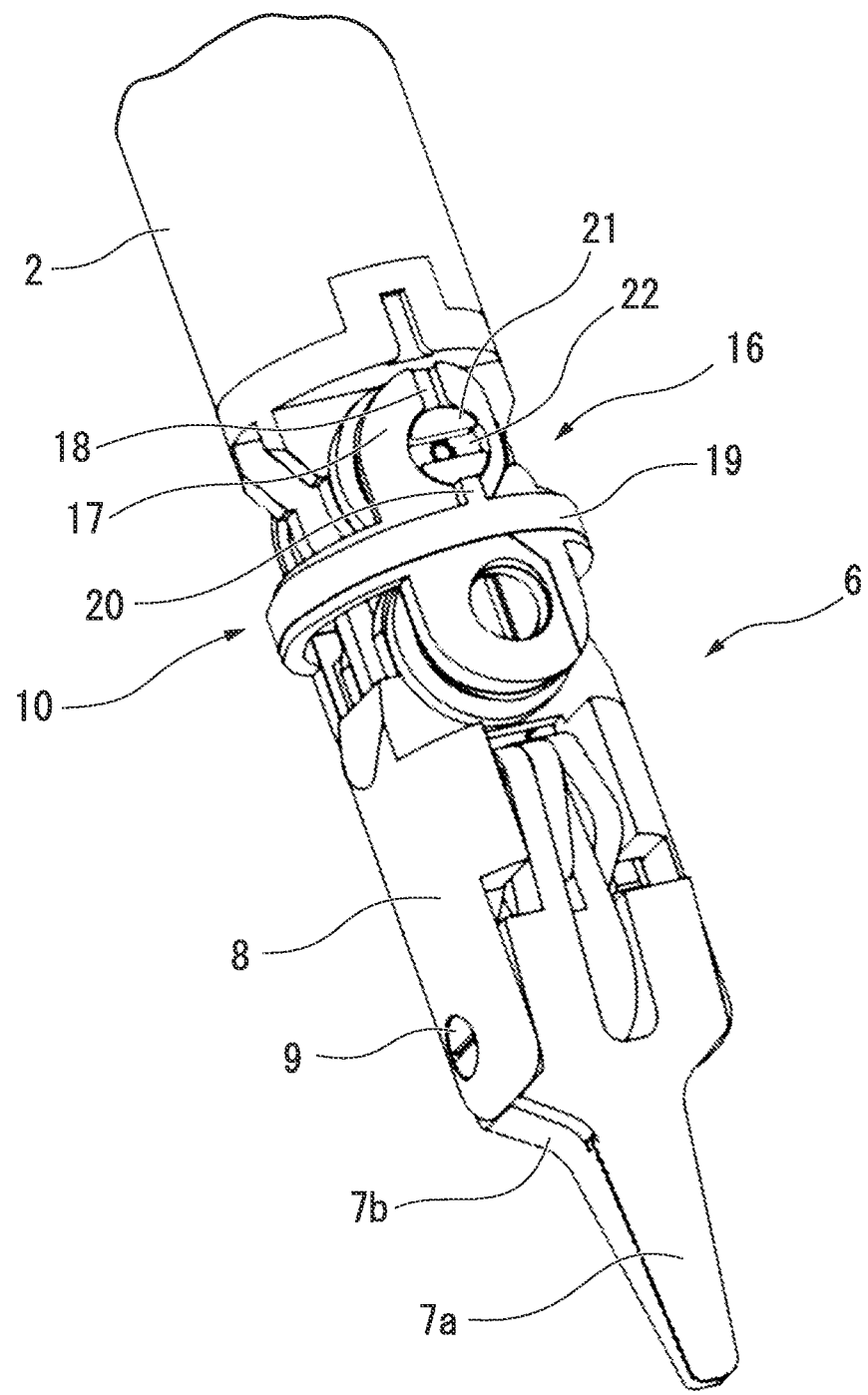
FIG. 2 is a perspective view of the configuration of one part of the surgical instrument.
Figure 3:
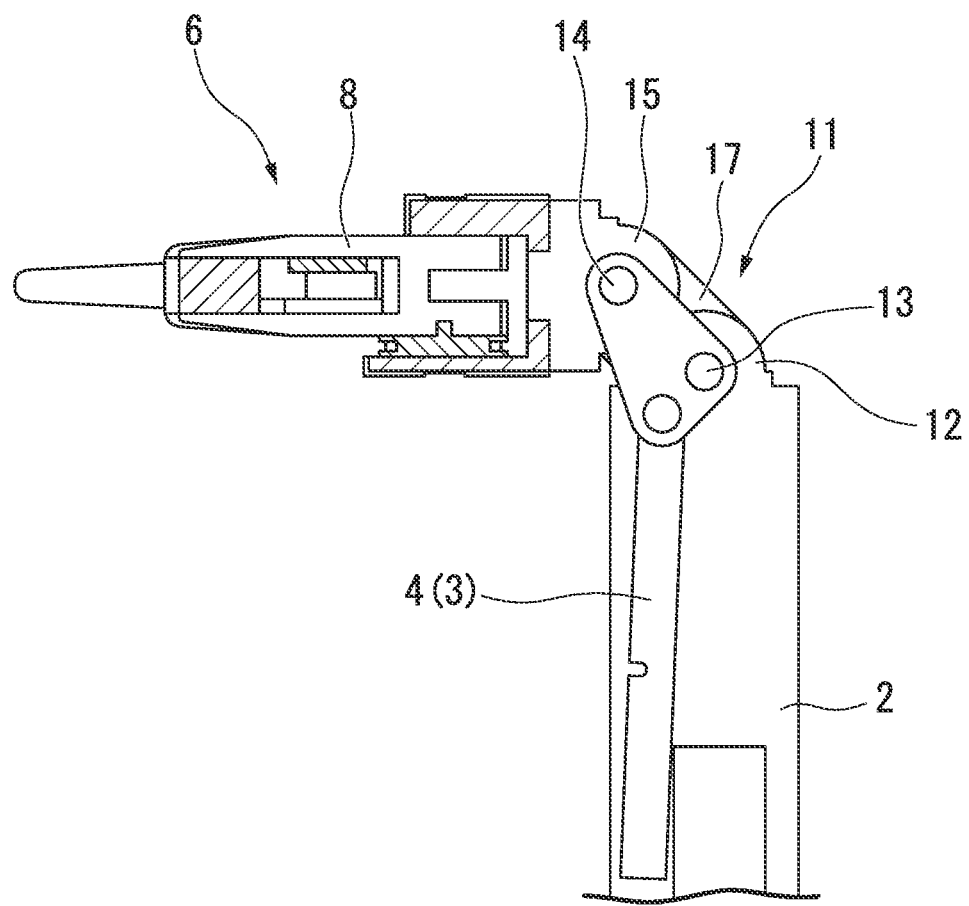
FIG. 3 is an explanatory view of the configuration of one part of the surgical instrument.
Figure 4:
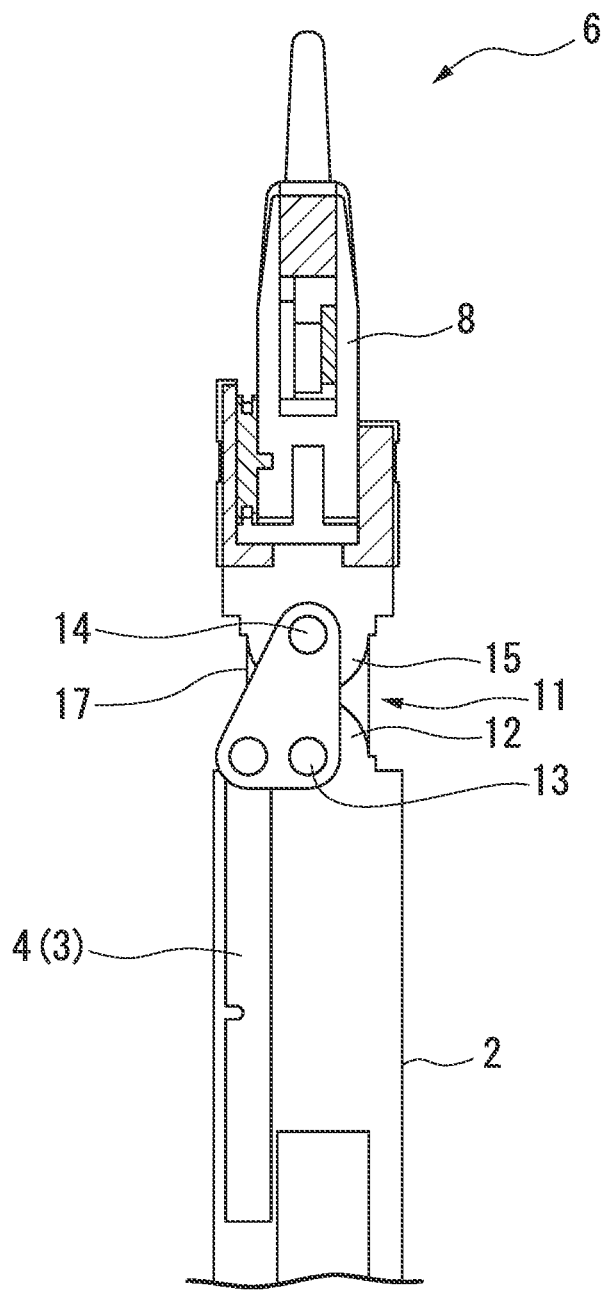
FIG. 4 is an explanatory view of the configuration of one part of the surgical instrument.
Figure 5:
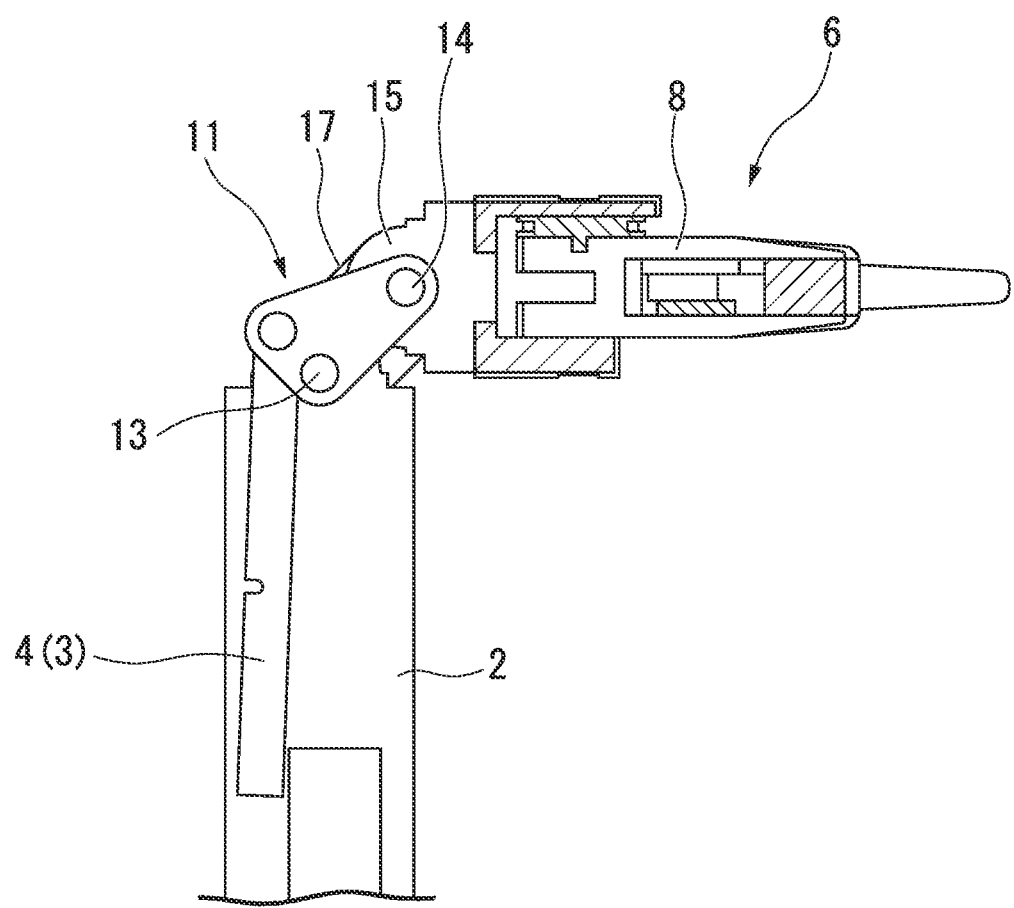
FIG. 5 is an explanatory view of the configuration of one part of the surgical instrument.
Figure 6:
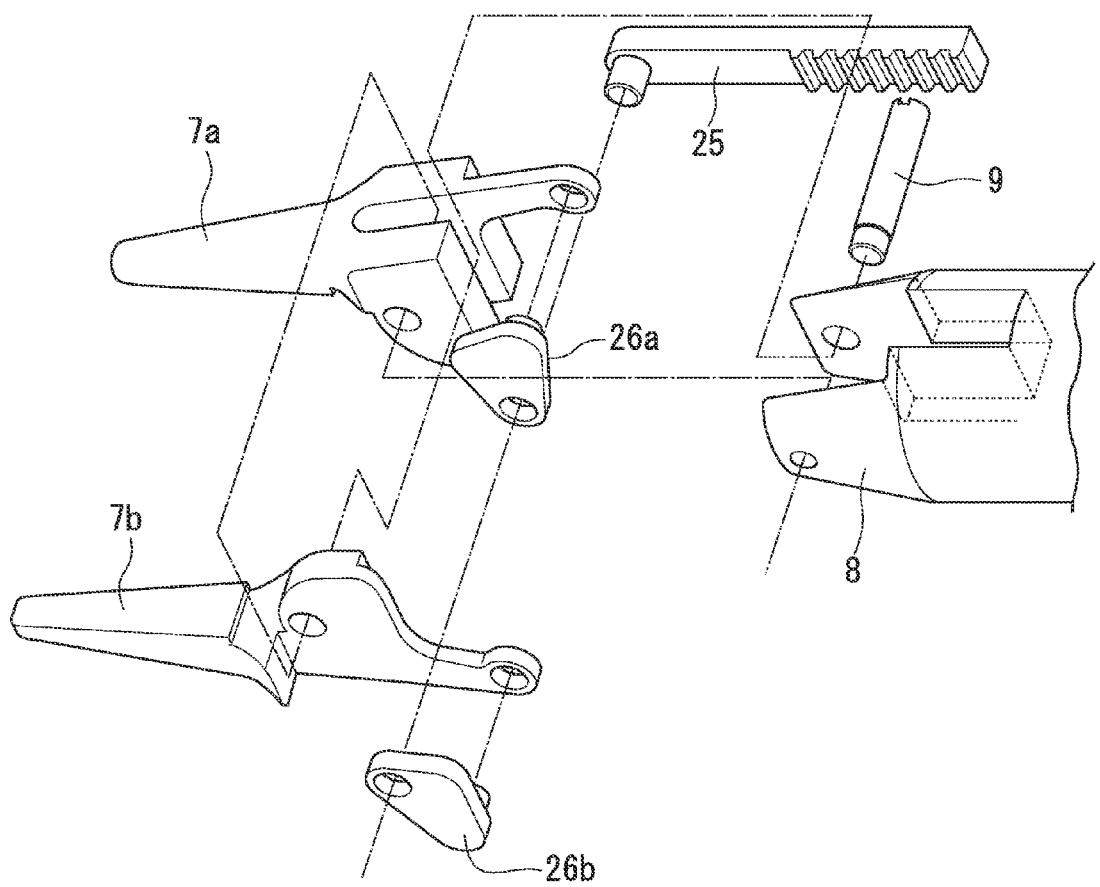
FIG. 6 is an exploded perspective view of the configuration of a treatment part of the surgical instrument.
Figure 7:
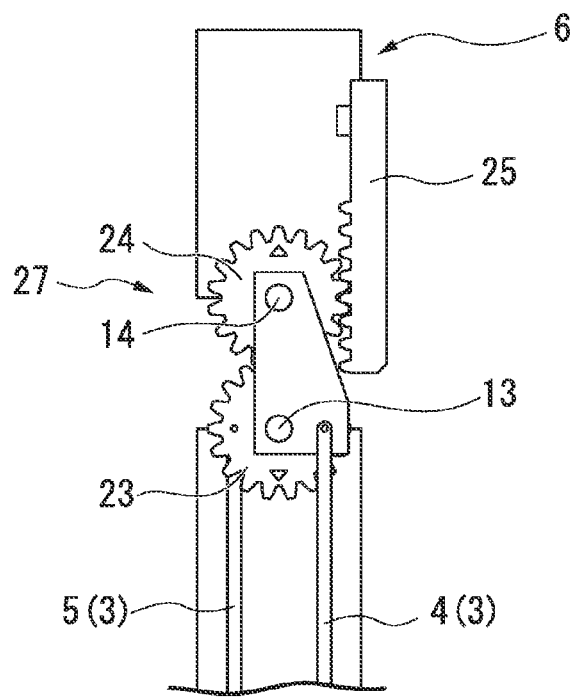
FIG. 7 is an explanatory view of a bend operation of a treatment part of the surgical instrument.
Figure 8:
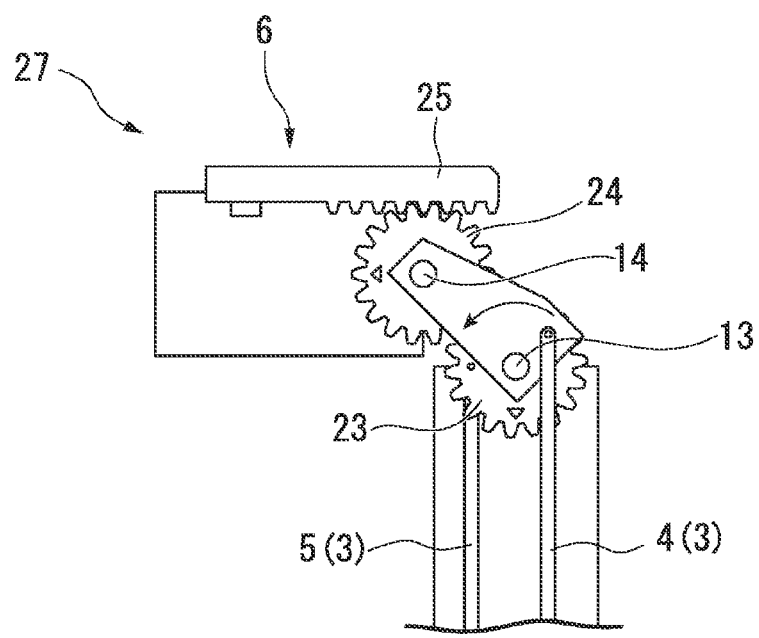
FIG. 8 is an explanatory view of a bend operation of a treatment part of the surgical instrument.
Figure 9:
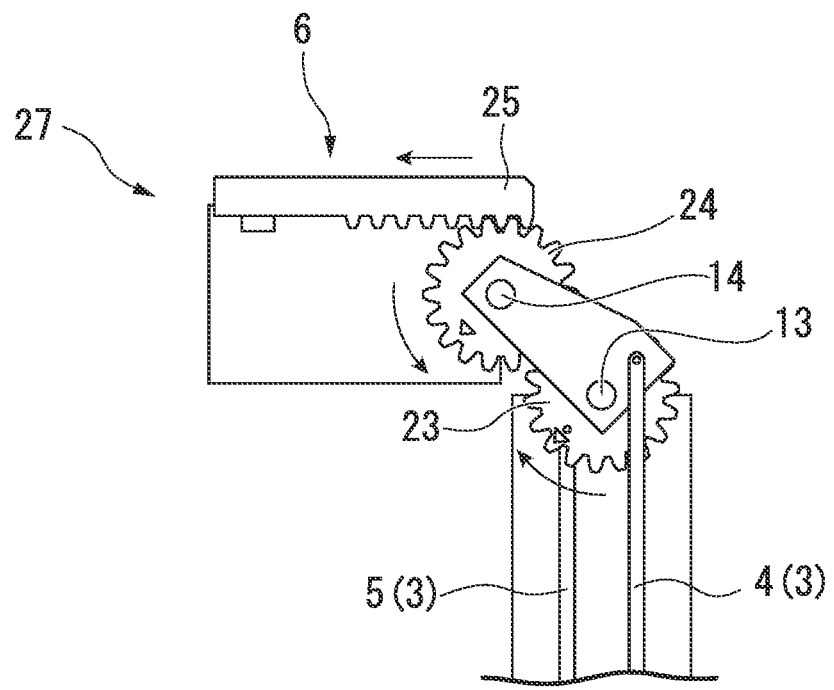
FIG. 9 is an explanatory view of a bend operation of a treatment part of the surgical instrument.
Figure 10:
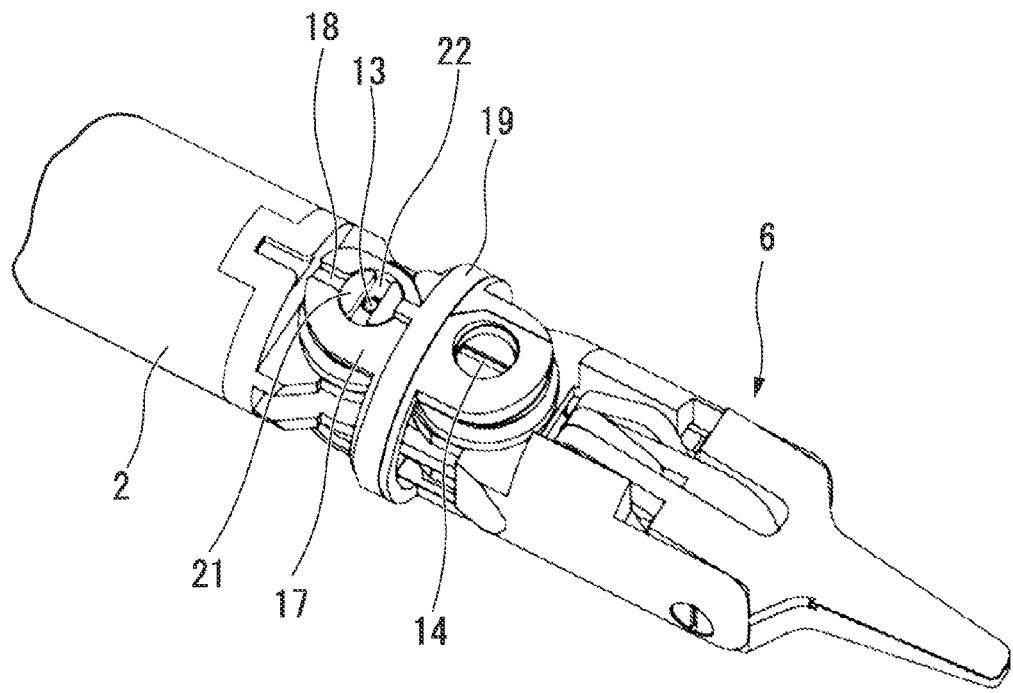
FIG. 10 is an explanatory perspective view of an operation of attaching and detaching a treatment part provided to the surgical instrument.

A surgical instrument 1 and a medical manipulator 100 according to one embodiment of the present invention will be explained. FIG. 1 is an overall view of a medical manipulator including a surgical instrument of the embodiment. FIG. 2 is a perspective view of the configuration of one part of the surgical instrument. FIGS. 3 to 5 are explanatory views of the configuration of one part of the surgical instrument. FIG. 6 is an exploded perspective view of the configuration of a treatment part on the surgical instrument. FIGS. 7 to 9 are explanatory views of a bend operation of a treatment part on the surgical instrument. FIGS. 3 to 5 and FIGS. 7 to 9 are explanatory schematic views of the configuration of the embodiment, and in some cases do not accurately depict the shapes of the members.

The surgical instrument 1 is attached to the medical manipulator 100 as one part thereof.

Firstly, the configuration of the medical manipulator 100 of the embodiment will be explained. As shown in FIG. 1, the medical manipulator 100 includes a master manipulator 101, a control device 110, and a slave manipulator 120.

The master manipulator 101 functions as a master for transmitting the movements of the operations performed by the surgeon to the slave manipulator 120, and includes a master display unit 102 such as a liquid crystal display device, and an operation unit 103 which the surgeon grasps and operates. Operations performed to the operation unit 103 of the master manipulator 101 are input to the control device 110.

The control device 110 includes a master-side control device 111 that receives the input from the master manipulator 101, and a slave-side control device 112 that outputs a drive signal to the slave manipulator 120.

Based on the input from the master manipulator 101, the master-side control device 111 generates an operating command for operating the slave manipulator 120, and outputs it to the slave-side control device 112.

Based on the operating command from the master-side control device 111, the slave-side control device 112 generates a drive signal for driving the slave manipulator 120, and outputs it to the slave manipulator 120.

The slave manipulator 120 includes a slave arm 121 that operates in compliance with the drive signal from the slave-side control device 112. The surgical instrument 1 of this embodiment is attached to this slave arm 121. In addition to the surgical instrument 1 of this embodiment, a treatment instrument for performing surgery, an endoscope, and such like, can be attached to the slave manipulator 120.

Subsequently, the configuration of the surgical instrument 1 will be explained.

The surgical instrument 1 is a medical instrument for performing treatment to a treatment target portion. As shown in FIGS. 1 and 2, the surgical instrument 1 includes an elongated member 2, a treatment part 6, a connection part 10, and a drive control unit 45.

In the explanation hereinafter, the side of the surgical instrument 1 including the treatment part 6 will be referred to as the distal side, and the side of the surgical instrument 1 including the drive control unit 45 will be referred to as the proximal side.

The elongated member 2 is a cylindrical member with a long axis. The elongated member 2 may be flexible or rigid depending on the configuration of the slave arm 121 that it is attached to. In the embodiment, the elongated member 2 is rigid.

As shown in FIGS. 3 and 7, a connecting rod 3 (moving member) for moving the treatment part 6 is disposed inside the elongated member 2. The connecting rod 3 includes a rod for bending 4, one end of which is connected to a double joint for bending 11 described below and another end of which is connected to the drive control unit 45, and a rod for opening-closing 5, one end of which is connected to a joint for opening-closing 27 described below and another end of which is connected to the drive control unit 45.

The treatment part 6 is provided for treating the treatment target portion. In the embodiment, as shown in FIGS. 2 and 6, the treatment part 6 is a forceps including a pair of forceps pieces 7a and 7b capable of opening and closing, and a cover 8 that holds the forceps pieces 7a and 7b. The pair of forceps pieces 7a and 7b are connected to each other by a shaft-shaped member 9 that forms their turning axis.

The connection part 10 connects the elongated member 2 and the treatment part 6. The connection part 10 includes a double joint for bending 11 for bending the treatment part 6 with respect to the elongated member 2, and a joint for opening-closing 27 (joint for operating treatment tool piece) for opening and closing the forceps pieces 7a and 7b.

The double joint for bending 11 includes a first fitting-cogs part 12 (first rolling guide part) fixed to the distal end of the elongated member 2, a first turning axis part 13 connected to the distal end of the elongated member 2, a second turning axis part 14 that extends parallel with the first turning axis part 13 and is connected to the treatment part 6, a second fitting-cogs part 15 (rolling guide part; second rolling guide part) fixed to the treatment part 6, and an engaging part 16 that switches the connecting state of the treatment part 6 and the elongated member 2.

The first fitting-cogs part 12 has gear-like dent provided in a circle around (circular-arc-shaped part) the center of turning of the first turning axis part 13. The second fitting-cogs part 15 has gear-like dent provided in a circle around (circular-arc-shaped part) the center of turning of the second turning axis part 14, and interlocks with the first fitting-cogs part 12. The cogs of the first fitting-cogs part 12 and the second fitting-cogs part 15 are provided in circles of equal radii, so that their relationship is set at a ratio of 1:1.

The second fitting-cogs part 15 can rotate while moving along the circumference of the first fitting-cogs part 12. Incidentally, plate-like members that move relatively with contact between their outer peripheral parts due to friction may be provided instead of the first fitting-cogs part 12 and the second fitting-cogs part 15.

While in the embodiment, the configuration is one where the first fitting-cogs part 12 and the second fitting-cogs part 15 are brought into frictional contact through the interlocking of cogs, the configuration need not be limited to this. For example, instead of frictional contact through interlocking of cogs, the configuration can be a mechanism that enables two rotating bodies to rotate and roll smoothly, such as one where two rubber rollers with no interlocking cogs (and large friction) are brought into frictional contact.

The first turning axis part 13 and the second turning axis part 14 are parallel with each other and have centers of turning that extend orthogonal to the extension line of the long axis of the elongated member 2.

As shown in FIG. 2, the engaging part 16 includes a main unit 17, a ring-shaped member 19, and a locking member 21.

The main unit 17 maintains a constant distance between the first fitting-cogs part 12 and the second fitting-cogs part 15. The rod for bending 4 of the connecting rod 3 is connected to the main unit 17. When the rod for bending 4 is advanced and retracted in the long-axis direction of the elongated member 2, the main unit 17 turns around the first turning axis part 13. As a result, the second turning axis part 14 swings around the first turning axis part 13.

The main unit 17 is connected to the first turning axis part 13 such that it can turn relative thereto and cannot be disconnected.

Moreover, the main unit 17 can engage with the second turning axis part 14 such that the treatment part 6 reaches a predetermined attachment direction with respect to the main unit 17, and can be attached and detached to/from the second turning axis part 14.

The main unit 17 is provided with a guide 18 for limiting the movement direction of the ring-shaped member 19. In the embodiment, the guide 18 has a groove formed in the outer face of the main unit 17 and extending in one direction. A protrusion 20 is formed on the ring-shaped member 19 and fits into the groove that forms the guide 18. The ring-shaped member 19 thus moves along the groove.

The ring-shaped member 19 is provided separately from the main unit 17, and binds it and the second turning axis part 14. That is, one part of the main unit 17 and one part of the second turning axis part 14 are inserted into the ring-shaped member 19, and the ring-shaped member 19 binds the main unit 17 and the second turning axis part 14 together. The protrusion 20 is provided on the ring-shaped member 19, and fits into the groove (guide 18) formed in the main unit 17.

When the ring-shaped member 19 is arranged in a position where it binds the main unit 17 and the second turning axis part 14, the treatment part 6 is in a state of being connected to the elongated member 2 (hereinafter 'bound state'). When the ring-shaped member 19 is arranged in a position deviated from the position where it binds the main unit 17 and the second turning axis part 14, the treatment part 6 is in a state where it can be detached from the elongated member 2 (hereinafter 'released state').

The locking member 21 is provided for switching between the bound state and the released state. The locking member 21 includes a groove 22 that can communicate with the groove (guide 18) formed in the main unit 17. As one part of the guide 18 formed in the main unit 17, the groove 22 formed in the locking member 21 has the function of limiting the movement direction of the ring-shaped member 19.

The locking member 21 can turn around the center of turning of the first turning axis part 13. When a rotational force around the center of turning of the first turning axis part equal to or greater than a predetermined level has acted as an external force against the locking member 21, the locking member 21 can turn around the center of turning of the first turning axis part 13 relative to the main unit 17. That is, by rotating the locking member 21, an operator can rotate the locking member 21 relative to the main unit 17, and switch the communicating state between the groove 22 formed in the locking member 21 and the guide 18 formed in the main unit 17. In a state where the abovementioned external force for rotating the locking member 21 is not being applied, the locking member 21 integrally operates the main unit 17.

When the groove 22 formed in the locking member 21 and the guide 18 formed in the main unit 17 are in the communicating state, the ring-shaped member 19 can move freely along the groove 22 formed in the locking member 21 and the guide 18 formed in the main unit 17. When the groove 22 formed in the locking member 21 and the guide 18 formed in the main unit 17 are in a non-communicating state, the ring-shaped member 19 cannot enter the groove 22 formed in the locking member 21. Therefore, when the groove 22 formed in the locking member 21 and the guide 18 formed in the main unit 17 are in the non-communicating state in the bound state mentioned above, the treatment part 6 is held in the bound state with respect to the elongated member 2.

As shown in FIGS. 6 to 9, the joint for opening-closing 27 includes a first gear for opening-closing 23 (first rolling guide part; first operation turning member) that is connected to the rod for opening-closing 5 and turns coaxially with the first turning axis part 13, a second gear for opening-closing 24 (rolling guide part; second rolling guide part; second operation turning member) that interlocks with the first gear for opening-closing 23 and turns coaxially with the second turning axis part 14, a rack 25 connected to the second gear for opening-closing 24, a link element 26a that connects the rack 25 to the forceps piece 7a, and a link element 26b that connects the rack 25 to the forceps piece 7b.

While in the embodiment, the first gear for opening-closing 23 and the second gear for opening-closing 24 are brought into frictional contact through the interlocking of cogs, the configuration need not be limited to this. For example, instead of frictional contact through interlocking of cogs, the configuration may be a mechanism that enables two rotating bodies to rotate and roll smoothly, such as one where two rubber rollers with no interlocking cogs (and large friction) are brought into frictional contact.

The link elements 26a and 26b shown in FIG. 6 transmit a pulling force, which comes from the rod for opening-closing 5 via first gear for opening-closing 23 and the second gear for opening-closing 24 shown in FIG. 7, through the rack 25. The link elements 26a and 26b convert the advancing-retracting operation of the rack 25 to an opening-closing operation of the forceps pieces 7a and 7b.

In the embodiment, the link element 25 of the joint for opening-closing 27 constitutes a toggle mechanism, with the grasping force of the forceps pieces 7a and 7b increasing exponentially as they move in the closing direction.

The drive control unit 45 shown in FIG. 1 includes an actuator 46 that advances and retracts the connecting rod 3 (rod for bending 4 and rod for opening-closing 5) in the long-axis direction of the elongated member 2, and a detection unit 47 that detects the amount of movement of the actuator 46. The drive control unit 45 operates in compliance with a drive signal output from the slave-side control device 112. The detection unit 47 detects the amount of movement of the actuator 46 and outputs to the slave-side control device 112. Thus the movement of the actuator 46 of the drive control unit 45 is feedback-controlled.

Subsequently, the effects of the surgical instrument 1 and the medical manipulator 100 of this embodiment will be explained, focusing on the operating principles and effects of the surgical instrument 1.

The surgical instrument 1 is used in the state where the treatment part 6 and the elongated member 2 are connected at the double joint for bending 11 and the joint for opening-closing 27. It is also possible to detach the treatment part 6 from the elongated member 2, and to attach another treatment part 6 to the elongated member 2. For example, treatment can be performed while switching among different types of treatment parts 6, and a treatment part 6 that has suffered an operational malfunction or the like can be replaced with a new treatment part 6 so that treatment can be continued.

The effects when using the surgical instrument 1 will be explained.

The double joint for bending 11 can be operated by using the actuator 46 to advance and retract the rod for bending 4. The joint for opening-closing 27 can be operated independently from the double joint for bending 11 by using the actuator 46 to advance and retract the rod for opening-closing 5.

The effects of the double joint for bending 11 will be explained.

If the rod for bending 4 is advanced and retracted without advancing and retracting the rod for opening-closing 5, as shown in FIGS. 3 and 5, the second turning axis part 14 turns around the first turning axis part 13. At this time, since the second fitting-cogs part 15 is interlocked with the first fitting-cogs part 12 provided on the double joint for bending 11, the second fitting-cogs part 15 turns around the second turning axis part 14. As the second turning axis part 14 swings around the first turning axis part 13 and the second fitting-cogs part 15 turns around the second turning axis part 14, the direction of the pair of forceps pieces 7a and 7b on the treatment part 6 changes. The pair of forceps pieces 7a and 7b do not open or close at this time.

In this case, at the double joint for bending 11, the main unit 17 is moved at an angle corresponding to the ratio between the radius of the first fitting-cogs part 12 and the radius of the second fitting-cogs part 15.

For example, when r1 is the radius of the first fitting-cogs part 12, r2 is the radius of the second fitting-cogs part 15, $\phi$ is the rotation angle of the main unit 17, and $\phi$ is the rotation angle of the treatment part 6, then $$r2(\phi-\theta)=r1\theta \tag{1}$$

$$\phi=\{(r1+r2)/r2\}\theta \tag{2}$$

For example, when the ratio between radius r1 of the first fitting-cogs part 12 and the radius r2 of the second fitting-cogs part 15 is 1:1 (r1=r2) as it is in this embodiment, this gives:

$$\theta=2\theta.$$

Therefore, when the main unit 17 is moved 45-degrees around the first turning axis part 13, the second fitting-cogs part 15 provided on the treatment part 6 side tilts 90-degrees with regard to the first fitting-cogs part 12. That is, this is an acceleration mechanism that makes it possible to reduce the amount of angular movement of the main unit 17 with respect to the amount of angular movement of the treatment part 6.

Subsequently, the effects when the treatment part 6 is made detachable from the elongated member 2 will be explained.

FIGS. 10 to 14 are explanatory perspective views of an operation of attaching and detaching the treatment part 6.

Figure 11:
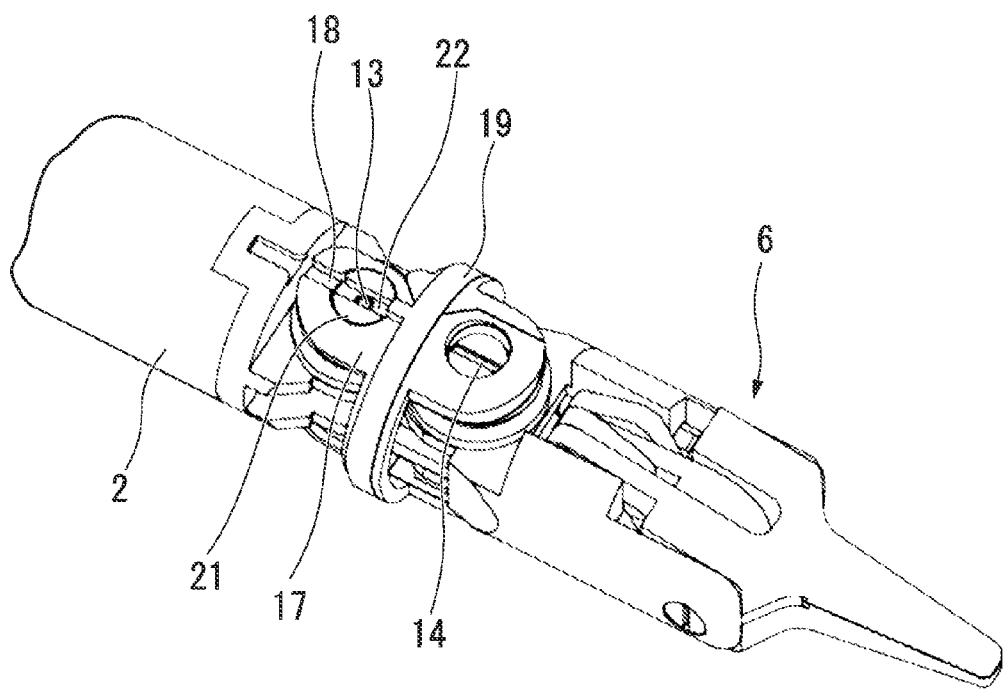
FIG. 11 is an explanatory perspective view of an operation of attaching and detaching a treatment part provided to the surgical instrument.

When it becomes necessary to detach the treatment part 6 from the elongated member 2, the locking member 21 is rotated relative to the main unit 17, whereby the groove 22 formed in the locking member 21 and the guide 18 formed in the main unit 17 are changed from the non-communicating state (see FIG. 10) to the communicating state (see FIG. 11). This has an effect of, for example, making it easier to insert a flat-blade screwdriver into the groove 22 formed in the locking member 21 and rotating the locking member 21.

Figure 12:
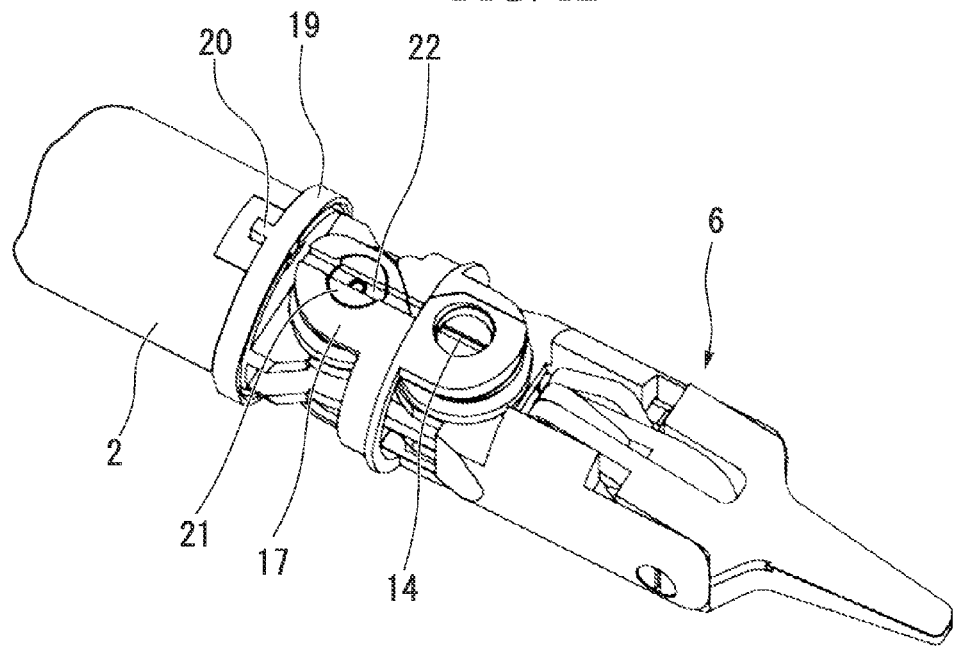
FIG. 12 is an explanatory perspective view of an operation of attaching and detaching a treatment part provided to the surgical instrument.
Figure 13:
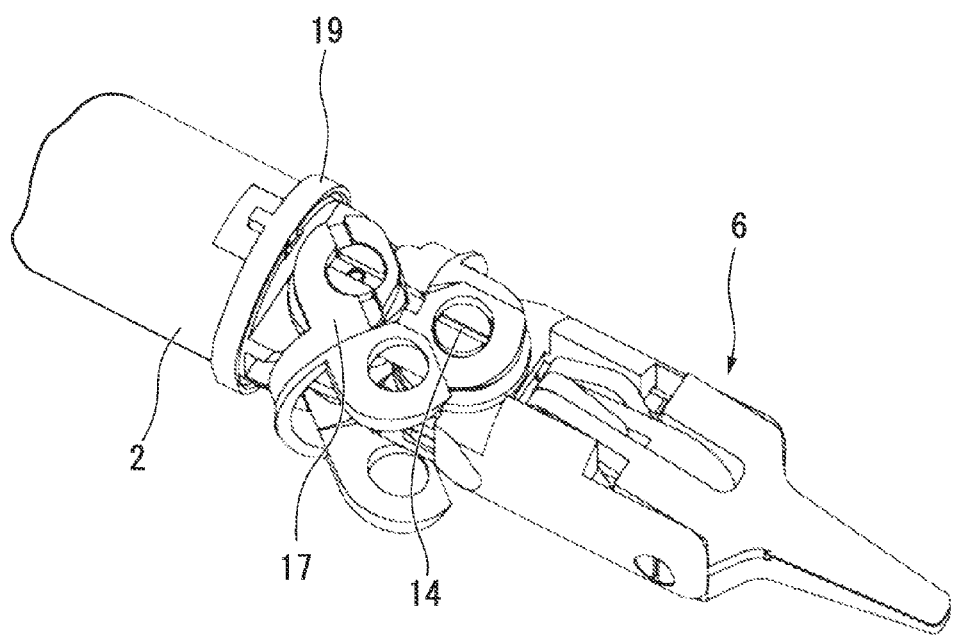
FIG. 13 is an explanatory perspective view of an operation of attaching and detaching a treatment part provided to the surgical instrument.
Figure 14:
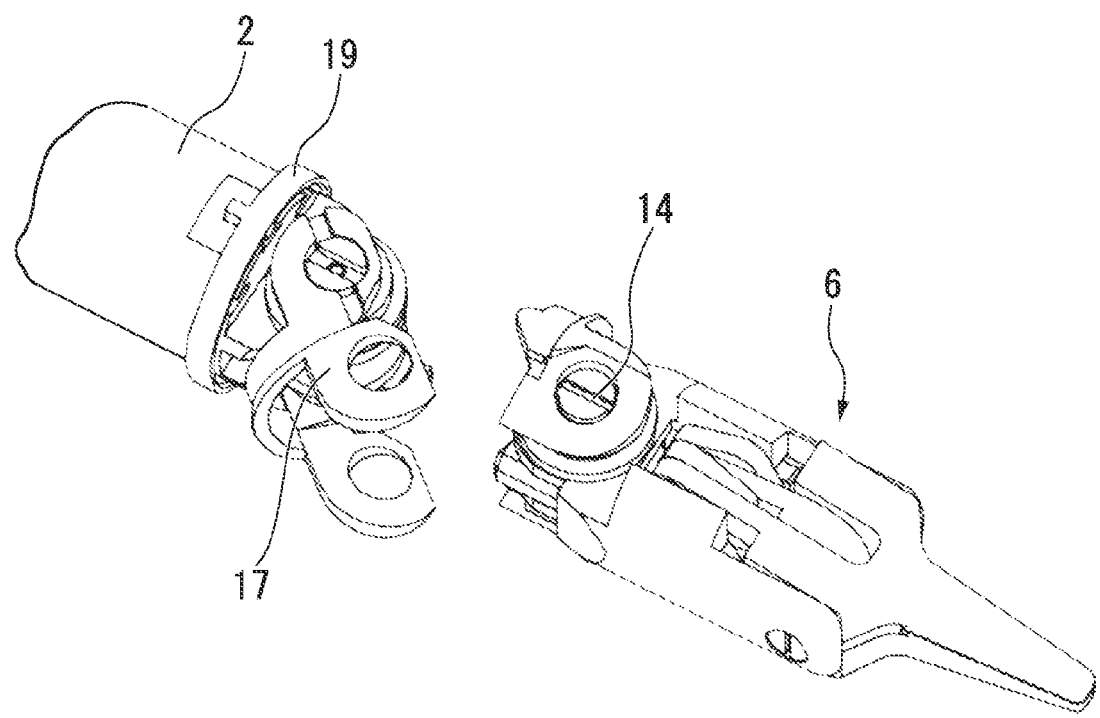
FIG. 14 is an explanatory perspective view of an operation of attaching and detaching a treatment part provided to the surgical instrument.

When the groove 22 formed in the locking member 21 and the guide 18 formed in the main unit 17 are in the communicating state, the ring-shaped member 19 can move along the groove 22 in the locking member 21 from the second turning axis part 14 side to the first turning axis part 13 side. As shown in FIG. 12, when the operator moves the ring-shaped member 19 to the first turning axis part 13 side, the second turning axis part 14 and the main unit 17 are unbound, and, as shown in FIGS. 13 and 14, the second turning axis part 14 and the treatment part 6 connected to the second turning axis part 14 are detached from the main unit 17.

In the embodiment, whatever the bend state of the double joint for bending 11, and whatever the open-close state of the joint for opening-closing 27, the treatment part 6 can be detached from the elongated member 2.

Another treatment part 6 can then be attached, or the detached treatment part 6 can be cleaned before re-attaching it.

When attaching the treatment part 6 to the elongated member 2, the treatment part 6 is positioned such that the first fitting-cogs part 12 interlocks with the second fitting-cogs part 15 and the first gear for opening-closing 23 interlocks with the second gear for opening-closing 24, the second turning axis part 14 is made to engage with the main unit 17, and the ring-shaped member 19 is used to bind the second turning axis part 14 and the main unit 17 together. Thereafter, the locking member 21 is rotated with respect to the main unit 17 so that the groove 22 formed in the locking member 21 and the guide 18 formed in the main unit 17 are in the non-communicating state.

It thus becomes possible to use the treatment part 6 attached to the elongated member 2.

Generally, to prevent infection, a medical manipulator is washed and disinfected each time surgery is performed.

For example, in the case of the medical manipulator described in Japanese Unexamined Patent Application, First Publication No. 2001-277157, the treatment part can be made detachable from the slave manipulator, and maintenance such as washing and disinfection is therefore easy. However, since a great many components are required to realize a configuration that enables the treatment part to be made detachable, the treatment part of the medical manipulator described in Japanese Unexamined Patent Application, First Publication No. 2001-277157 has a complex structure, and cannot be said to be easier to wash.

In contrast, according to the surgical instrument 1 and the medical manipulator 100 of this embodiment, since the main unit 17 and the second turning axis part 14 are bound by the ring-shaped member 19, the treatment part 6 can be made detachable from the elongated member 2 with a simple configuration.

Also, according to the surgical instrument 1 and the medical manipulator 100 of this embodiment, the increase in the number of components for attaching and detaching the treatment part 6 is less than that of the art described in surgical instrument 1.

Since the treatment part 6 is made detachable from the elongated member 2 by attaching and detaching the first turning axis part 13 to and from the second turning axis part 14, the components of the joint section for changing the direction of the treatment part 6 with respect to the elongated member 2 can be for making the treatment part 6 detachable. Therefore, in the surgical instrument 1 and the medical manipulator 100 of the embodiment, the number of components is not considerably greater than a configuration where the treatment part 6 is not detachable.

MODIFIED EXAMPLE 1

Figure 15:
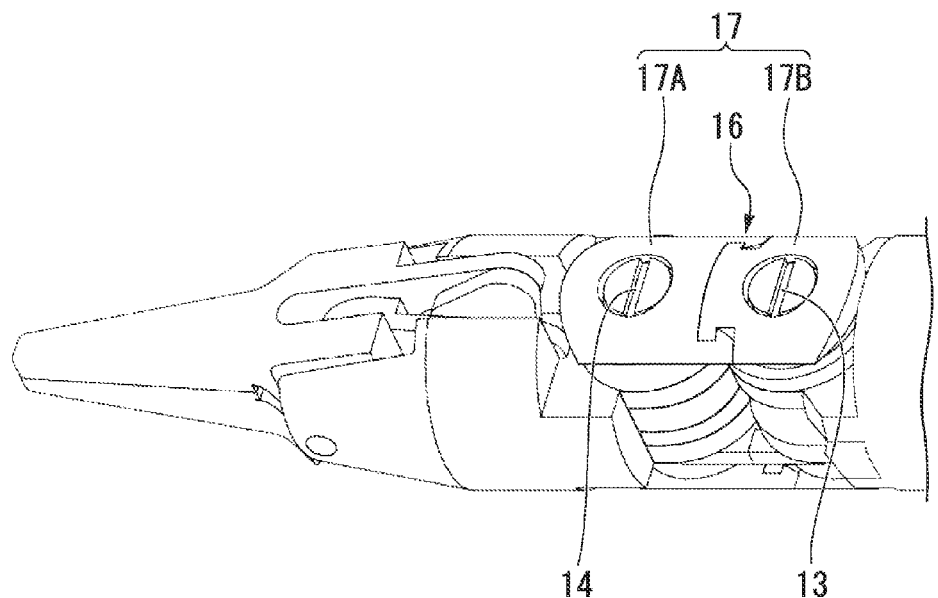
FIG. 15 is a perspective view of the configuration of a modified example of the embodiment.
Figure 16:
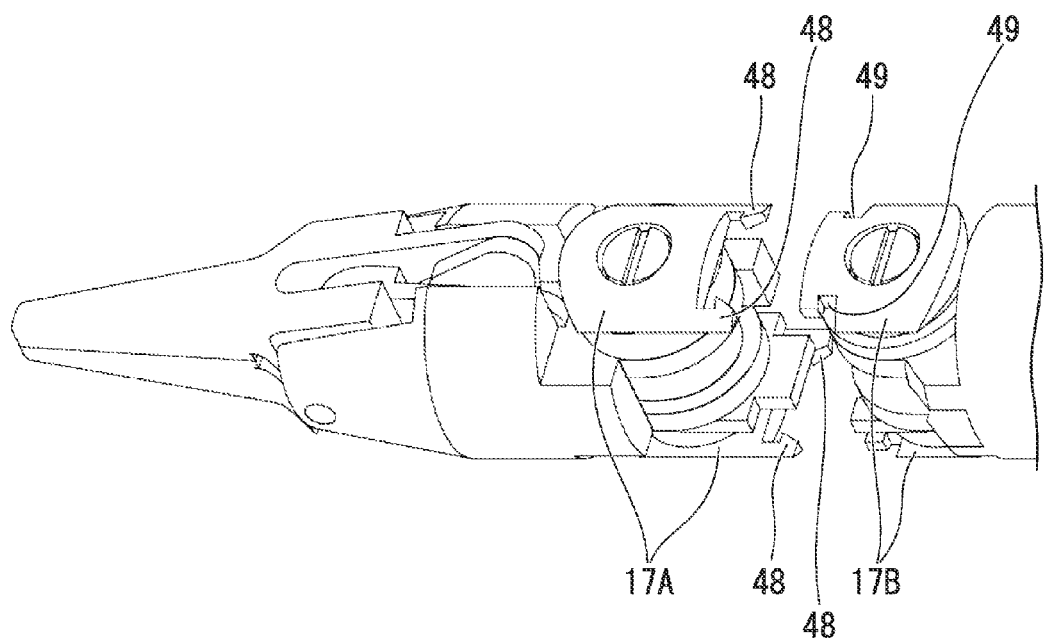
FIG. 16 is an explanatory perspective view of an effect of the modified example.

Subsequently, a modified example of the embodiment will be explained. FIG. 15 is a perspective view of the configuration of the modified example. FIG. 16 is an explanatory perspective view of the effects of the modified example.

As shown in FIG. 15, in the modified example, instead of a configuration where the main unit 17 and the second turning axis part 14 can be attached and detached, the main unit 17 can be divided into distal members 17A and proximal members 17B.

As shown in FIGS. 15 and 16, claw parts 48 for engaging with the distal members 17A are formed on the distal members 17A. Recessed parts 49 for fitting the claw parts 48 therein are formed in the proximal members 17B. The claw parts 48 and the recessed parts 49 constitute an engaging part 16 that brings the first turning axis part 13 and the treatment part 6 into an engaged state, in the same manner as the engaging part 16 described in the embodiment above.

When the claw parts 48 of the distal members 17A are pressed into the recessed parts 49 of the proximal members 17B, the proximal members 17B and the distal members 17A elastically deform slightly, and the claw parts 48 enter the recessed parts 49. The treatment part 6 is thus engaged with the elongated member 2.

This configuration achieves effects similar to those of the embodiment described above.

In addition, the modified example has fewer components than the embodiment described above.

While in the embodiment including the modified example described above, the example of an operation of a treatment tool piece is one of opening and closing a pair of treatment tool pieces, namely the forceps pieces 7a and 7b, the configuration is not limited to that. For example, the operation can be one which is bending (turning) a single treatment tool piece. The treatment tool piece can be a medical instrument other than forceps pieces.

MODIFIED EXAMPLE 2

Figure 17:
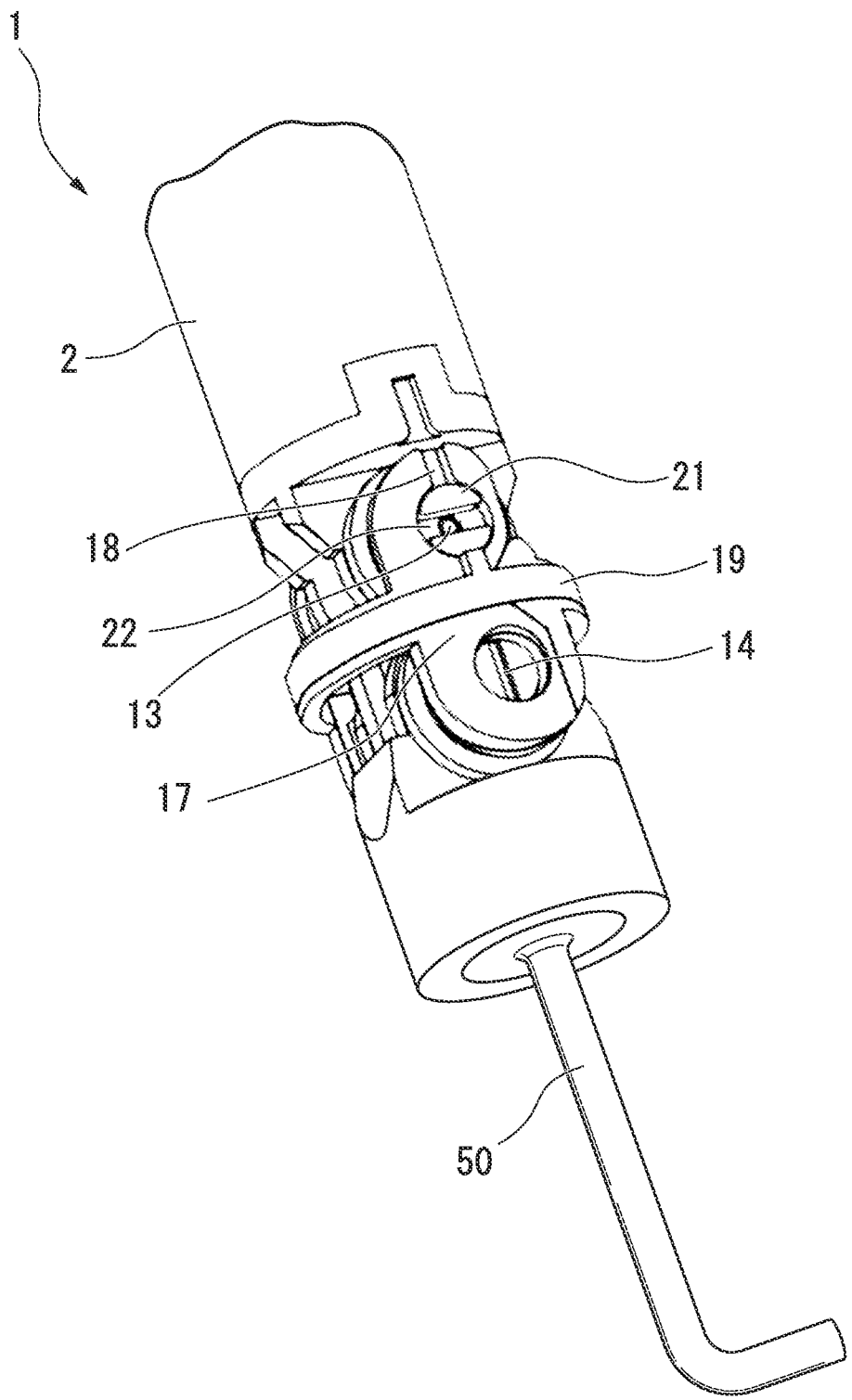
FIG. 17 is a perspective view of the configuration of another modified example of the embodiment.
Figure 18:
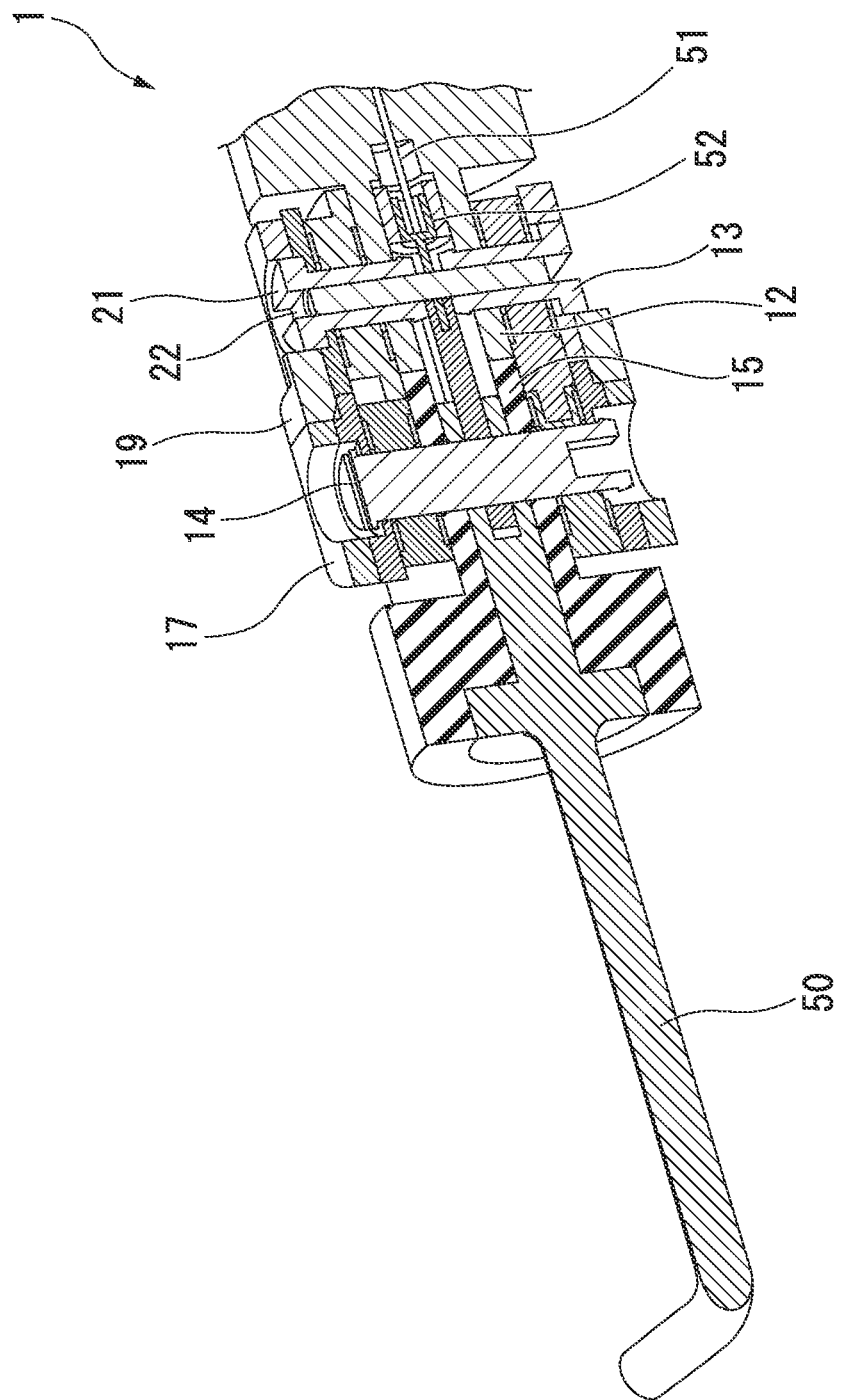
FIG. 18 is a cross-sectional view of the configuration of the modified example.

Subsequently, another modified example of the embodiment will be explained. FIG. 17 is a perspective view of the configuration of the modified example. FIG. 18 is an explanatory cross-sectional view of the configuration of the modified example.

As shown in FIGS. 17 and 18, instead of the treatment part 6 having the forceps pieces 7a and 7b, the modified example includes a treatment part 6 having an electric scalpel electrode 50.

The elongated member 2 includes a lead wire 51 that is electrically connected to the electric scalpel electrode 50. The lead wire 51 and the electrode 50 are detachably connected via a plug 52. The treatment part 6 of the modified example need not be connected to the joint for opening-closing 27, and need not include the joint for opening-closing 27. Also, in the modified example, the joint for opening-closing 27 and the rod for opening-closing 5 need not be provided.

This type of configuration achieves effects similar to those of the embodiment described above.

While an embodiment of the invention has been described in detail with reference to the drawings, the specific configuration is not limited to this embodiment.

For example, it is acceptable to use a treatment part that bends at the first turning axis part and does not include the second turning axis part described above.

Various other additions, omissions, substitutions, and other changes can be made to the configuration without deviating from the main points of the invention.

The invention is not limited to the forgoing description, and is limited only by the accompanying claims.

What is claimed is:

1. A surgical instrument for performing treatment to a treatment target portion, the surgical instrument comprising:
   a cylindrical elongated member having a long axis;
   a treatment part connected to the elongated member; and
   a connection part that detachably connects the elongated member to the treatment part, wherein
   the connection part comprises:
   a first turning axis part provided to the elongated member;
   a second turning axis part provided to the treatment part;
   a first rolling guide part that is provided to the elongated member and includes a circular-arc-shaped part coaxial with the first turning axis part;
   a second rolling guide part that is provided to the treatment part and includes a rolling guide part having a circular-arc-shaped part coaxial with the second turning axis part, the rolling guide part rollingly contacting the first rolling guide part;
   an engaging part that brings the treatment part and the elongated member into an engaging state, and
   the connection part is detachable between the first turning axis part and the second turning axis part;
   wherein the engaging part comprises:
   a main unit that is connected to the first turning axis part and is capable of engaging with the second turning axis part;
   a ring-shaped member that is provided separately from the main unit, and binds the main unit together with the second turning axis part; and
   a locking member that switches between a bound state and a released state, wherein in the bound state, the ring-shaped member is arranged in a position where it binds the main unit and the second turning axis part, and in the released state, the ring-shaped member is arranged in a position deviated from the position where it binds the main unit and the second turning axis part.

2. The surgical instrument according to claim 1, wherein the main unit is provided with a groove that engages with the ring-shaped member and defines its movement direction;
   the locking member is provided with a groove and is capable of moving relative to the main unit;
   when the groove provided in the locking member and the groove provided in the main unit are in a communicating state, the ring-shaped member is capable of switching between the released state and the bound state; and
   when the groove provided in the locking member and the groove provided in the main unit are in a non-communicating state, the treatment part is held in the bound state with respect to the elongated member.

3. The surgical instrument according to claim 1, further comprising:
   a treatment tool piece provided on the treatment part and is capable of operating;
   a joint for operating the treatment tool piece that connects the elongated member to the treatment tool piece; and
   a moving member that is connected to the joint for operating the treatment tool piece in order to operate the treatment tool piece, wherein
   the joint for operating the treatment tool piece comprises:
   a first operation turning member that is connected to the moving member and turns around a predetermined center of turning;
   a second operation turning member that is connected to the first operation turning member such that it turns in the opposite direction relative to the first operation turning member coaxial with the second turning axis part or around a center of turning that is nearer to the first turning axis part than the second turning axis part; and a link that converts a rotational force of the second operation turning member to an operation of the treatment tool piece;

the joint for operating treatment tool piece is detachable between the first operation turning member and the second operation turning member by being detachable from the connection part.

4. The surgical instrument according to claim 3, wherein the treatment tool piece comprises a pair of treatment tool pieces, and the operation of the treatment tool pieces is an operation of opening and closing the pair of treatment tool pieces.

5. A medical manipulator comprising:
the surgical instrument according to claim 1;
a slave manipulator including at least one joint, the surgical instrument being attached to the slave manipulator; and
a master manipulator that generates operating commands for driving the joint of the slave manipulator.

6. The surgical instrument according to claim 2, further comprising:
   a treatment tool piece provided on the treatment part and is capable of operating;
   a joint for operating the treatment tool piece that connects the elongated member to the treatment tool piece; and
   a moving member that is connected to the joint for operating the treatment tool piece in order to operate the treatment tool piece, wherein
   the joint for operating the treatment tool piece comprises:
   a first operation turning member that is connected to the moving member and turns around a predetermined center of turning;
   a second operation turning member that is connected to the first operation turning member such that it turns in the opposite direction relative to the first operation turning member coaxial with the second turning axis part or around a center of turning that is nearer to the first turning axis part than the second turning axis part; and a link that converts a rotational force of the second operation turning member to an operation of the treatment tool piece;

the joint for operating treatment tool piece is detachable between the first operation turning member and the second operation turning member by being detachable from the connection part.

7. The surgical instrument according to claim 6, wherein the treatment tool piece comprises a pair of treatment tool pieces, and the operation of the treatment tool pieces is an operation of opening and closing the pair of treatment tool pieces.

8. A medical manipulator comprising:
the surgical instrument according to claim 1;
a slave manipulator including at least one joint, the surgical instrument being attached to the slave manipulator; and
a master manipulator that generates operating commands for driving the joint of the slave manipulator.

9. A medical manipulator comprising:
the surgical instrument according to claim 2;
a slave manipulator including at least one joint, the surgical instrument being attached to the slave manipulator; and
a master manipulator that generates operating commands for driving the joint of the slave manipulator.

10. A medical manipulator comprising:
the surgical instrument according to claim 3;
a slave manipulator including at least one joint, the surgical instrument being attached to the slave manipulator; and
a master manipulator that generates operating commands for driving the joint of the slave manipulator.

11. A medical manipulator comprising:
the surgical instrument according to claim 4;
a slave manipulator including at least one joint, the surgical instrument being attached to the slave manipulator; and
a master manipulator that generates operating commands for driving the joint of the slave manipulator.

\* \* \* \* \*